(12) United States Patent
Moulton et al.

(10) Patent No.: US 7,750,166 B2
(45) Date of Patent: Jul. 6, 2010

(54) IONIC LIQUIDS CONTAINING A SULFONATE ANION

(75) Inventors: Roger Moulton, Austin, TX (US); James H. Davis, Jr., Mobile, AL (US)

(73) Assignees: University of South Alabama, Mobile, AL (US); Sachem, Inc., Austin, TX (US)

( * ) Notice: Subject to any disclaimer, the term of this patent is extended or adjusted under 35 U.S.C. 154(b) by 454 days.

(21) Appl. No.: 10/642,438

(22) Filed: Aug. 15, 2003

(65) Prior Publication Data

US 2005/0131118 A1   Jun. 16, 2005

Related U.S. Application Data

(60) Provisional application No. 60/404,178, filed on Aug. 16, 2002, provisional application No. 60/404,202, filed on Aug. 16, 2002.

(51) Int. Cl.
*C07C 233/00* (2006.01)
*C07D 233/02* (2006.01)
*C07D 295/00* (2006.01)

(52) U.S. Cl. ............... 548/300.1; 548/400; 564/123

(58) Field of Classification Search ............... 252/364, 252/182.2; 502/127, 150; 44/268; 524/158; 560/14, 150; 548/300.1, 400; 564/123
See application file for complete search history.

(56) References Cited

U.S. PATENT DOCUMENTS

| | | | |
|---|---|---|---|
| 2,072,085 A * | 3/1937 | Keiser et. al. ............... 516/151 |
| 2,181,087 A | 11/1939 | Caryl et al. |
| 2,446,331 A | 8/1948 | Hurley |
| 2,507,030 A | 5/1950 | Lynch et al. |
| 3,418,216 A | 12/1968 | Dotzer |
| 4,063,889 A * | 12/1977 | Kissa ............... 8/539 |
| 4,150,216 A * | 4/1979 | Quack et al. ............... 528/290 |
| 4,463,071 A | 7/1984 | Gifford et al. |
| 4,480,119 A * | 10/1984 | Longley et al. ............... 560/151 |
| 4,572,769 A | 2/1986 | Shimizu |
| 4,628,023 A | 12/1986 | Cawston et al. |
| 4,714,530 A | 12/1987 | Hale et al. |
| 4,764,440 A | 8/1988 | Jones et al. |
| 4,776,929 A | 10/1988 | Aoyama |
| 4,820,621 A | 4/1989 | Tanka et al. |
| 4,857,238 A | 8/1989 | Tsuchiya et al. |
| 4,882,244 A | 11/1989 | Donahue et al. |
| 4,913,828 A | 4/1990 | Caswell et al. |
| 4,915,854 A | 4/1990 | Mao et al. |
| 4,919,839 A | 4/1990 | Durbut et al. |
| 5,125,968 A * | 6/1992 | Takimoto et al. ......... 106/31.75 |
| 5,135,825 A | 8/1992 | Mori et al. |
| 5,273,840 A | 12/1993 | Dominey |
| 5,286,354 A | 2/1994 | Bard et al. |
| 5,415,857 A | 5/1995 | Robbins et al. |
| 5,543,522 A | 8/1996 | Kawahara et al. |
| 5,565,060 A | 10/1996 | Austin et al. |
| 5,683,832 A | 11/1997 | Bonhote et al. |
| 5,827,602 A | 10/1998 | Koch et al. |
| 5,853,555 A | 12/1998 | Sharifian et al. |
| 5,870,275 A | 2/1999 | Shiono et al. |
| 5,910,237 A | 6/1999 | Moulton et al. |
| 5,929,009 A | 7/1999 | Gambogi |
| 5,951,845 A | 9/1999 | Moulton |
| 5,965,054 A | 10/1999 | McEwen et al. |
| 5,968,338 A | 10/1999 | Hulme et al. |
| 5,981,474 A | 11/1999 | Manning et al. |
| 6,165,259 A | 12/2000 | Hallstrom et al. |
| 6,306,805 B1 * | 10/2001 | Bratescu et al. ............... 510/123 |
| 6,379,634 B1 | 4/2002 | Fields |
| 6,406,677 B1 | 6/2002 | Carter et al. |
| 6,468,495 B1 | 10/2002 | Fields |
| 2002/0010291 A1 | 1/2002 | Murphy |
| 2002/0015883 A1 | 2/2002 | Hilarius |
| 2002/0015884 A1 | 2/2002 | Schmidt |
| 2002/0055045 A1 | 5/2002 | Michot |

FOREIGN PATENT DOCUMENTS

| JP | 08-030013 | * | 2/1996 |
|---|---|---|---|
| JP | 11-072969 | | 3/1999 |

OTHER PUBLICATIONS

International Search Report, Application No. PCT/US03/25816, dated Oct. 21, 2004.

Freemantle; "Eyes on Ionic Liquids"; Chemical Engineering News Online; *Science/Technology*, May 15, 2000, vol. 78, No. 20, pp. 37-50.

Holbrey et al.; "Ionic Liquids"; *Clean Products and Processes 1* (1999) 223-236, 1999.

(Continued)

*Primary Examiner*—Taylor Victor Oh
(74) *Attorney, Agent, or Firm*—Foley Hoag LLP

(57) ABSTRACT

The present invention relates to novel ionic liquids comprising a docusate, docusate variant, or other sulfonate anion. The ionic liquids may be conveniently made via, for example, metathesis. The ionic liquids are often hydrophobic and useful in many hydrocarbon compositions, polymer compositions, and in supercritical carbon dioxide applications. The ionic liquids are capable of hindering static electricity buildup in the hydrocarbon compositions and can therefore minimize flammability and/or explosiveness.

7 Claims, No Drawings

OTHER PUBLICATIONS

Bradley, "Super Solvents"; ChemPros; *Technology Ireland*; Sep. 1999.
Seddon; "QUILL rewrites the future of industrial solvents"; *Green Chemistry*, 1999.
Chauvin; "Nonaqueous ionic liquids as reaction solvents"; *Chemtech*, Sep. 1995.
Welton; "Room-Temperature Ionic Liquids. Solvents for Synthesis and Catalysis"; *Chem Rev.*, 1999, 99, 2071-2083.

* cited by examiner

IONIC LIQUIDS CONTAINING A SULFONATE ANION

RELATED APPLICATION DATA

The present application claims priority to U.S. Provisional Application No. 60/404,178, filed Aug. 16, 2002 and U.S. Provisional Application No. 60/404,202, filed Aug. 16, 2002.

FIELD OF THE INVENTIONS

The present inventions pertain to compositions comprising an ionic liquid comprising a Docusate anion, a docusate variant anion, or other sulfonate anion, and processes for making said compositions.

BACKGROUND AND SUMMARY OF THE INVENTIONS

Ionic liquids are salts that are liquid at ambient or near ambient temperatures. Ionic liquids have a number of uses that include replacing organic solvents in chemical processes and reactions, extracting organic compounds from aqueous waste streams, and as electrolytes in devices such as capacitors and batteries. This is because, unlike conventional organic solvents, ionic liquids are non-volatile and non-flammable. These properties are advantageous to help reduce losses to evaporation, eliminate volatile organic emissions, and improve safety.

Other properties of ionic liquids have also proved advantageous. For example, many ionic liquids have a broad temperature range at which they remain liquid and also are stable over a broad pH range. This is beneficial for high temperature processes with a demanding pH. Further, some ionic liquid systems can be used as both a solvent and catalyst. For example, BMIM-$Al_2Cl_7$ and EMIM-$Al_2Cl_7$ can be employed as a solvent and catalyst in Friedel-Crafts reactions wherein BMIM is 1-butyl-3methylimidazolium and EMIM is 1-ethyl-3-methylimidazolium.

For the aforementioned reasons, it would be desirable to discover new ionic liquid compounds with advantageous properties. It would further be desirable if such compounds could be made by simple processes with low amounts of waste and impurities.

Advantageously, new ionic liquid compounds have been discovered. The compounds comprise either a docusate or other sulfonate anion and are made via simple processes that are capable of producing ionic liquids having a high purity.

DETAILED DESCRIPTION OF THE INVENTIONS

As used herein "ionic liquid" means a salt comprising a cation and an anion. The salt (or hydrate or solvate of the salt) is a liquid at ambient or near ambient temperatures (i.e., having a melting point, or melting range, less than about 100° C.). An ionic liquid may comprise two or more different salts, e.g., mixtures of salts comprising two or more different cations, anions, or both. The ionic liquids of the present inventions are often hydrated or solvated. Thus, both hydrates and solvates are considered to be within the definition of "ionic liquid."

As used herein "hydrophilic ionic liquid" means an ionic liquid which is partially or wholly miscible with water.

As used herein "hydrophobic ionic liquid" means an ionic liquid which is relatively immiscible with water, i.e., forms two phases at ambient conditions.

As used herein "composition" includes a mixture of the materials that comprise the composition, as well as, products formed by the reaction or the decomposition of the materials that comprise the composition.

As used herein "derived from" means made or mixed from the specified materials, but not necessarily composed of a simple mixture of those materials. Substances "derived from" specified materials may be simple mixtures of the original materials, and may also include the reaction products of those materials, or may even be wholly composed of reaction or decomposition products of the original materials.

As used herein "halo" means chloro, bromo, fluoro, or iodo, arylene means a divalent aromatic group such as phenylene, napthylenylene, biphenylene, antracenylene, phenanthrenylene, etc., heteroarylene means a divalent heteroaromatic group such as pyrrolene, furanylene, thiophenylene, pyridinylene, etc., alkylene means a divalent alkane group which may be substituted with one or more heteroatoms such as nitrogen or oxygen, cycloalkylene means a divalent cycloalkane group which may be substituted with one or more heteroatoms such as nitrogen or oxygen, alkenylene means a divalent alkene group which may be substituted with one or more heteroatoms such as nitrogen or oxygen.

As used herein "Docusate" is the anion of the bis(2-ethylhexyl)ester of sulfosuccinic acid. The chemical formula of Docusate (anion) is $C_{20}H_{37}O_7S^-$. As used herein, "docusate variant" is taken to include the compounds described by chemical structures I and III described below and includes the anions of bis(organo)ester derivatives of sulfosuccinic acid and anions of bis(organoamide) derivatives of sulfosuccinic acid.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The ionic liquid of the present invention comprise one or more compounds. Thus, the ionic liquid may be a pure compound or may be a mixture of compounds. Each compound comprises an anion or a mixture of anions and a cation or a mixture of cations as described below.

Anions

Exemplary anions of compounds of the instant invention include those having a chemical structure selected from

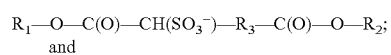
and                    I $R_1$, $R_2$, $R_4$ and $R_5$ in Structure I and II above are independently selected from the group consisting of substituted or unsubstituted alkyl or alkenyl groups. The alkyl or alkenyl

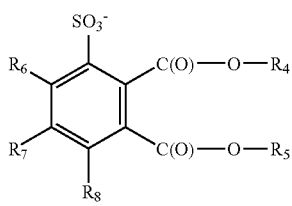

groups of $R_1$, $R_2$, $R_4$ and $R_5$ should have a sufficient number of carbon atoms so that the ionic liquid has the desired properties. For example, if a hydrophobic ionic liquid is desired then the total number of carbon atoms in the ionic liquid will typically be more than if a hydrophilic ionic liquid is desired. However, if there are too many carbon atoms in the anion then the ionic liquid may be less useful as an ionic liquid due to a decline in properties such as vapor pressure, dipole moment, polarity, etc.

For hydrophobic ionic liquids $R_1$, $R_2$, $R_4$ and $R_5$ are preferably independently selected from alkyl groups having about five or more carbon atoms, preferably from about six to about eighteen carbon atoms. One preferable group for $R_1$, $R_2$, $R_4$ and $R_5$ is —$CH_2$—$CH(CH_2CH_3)(CH_2CH_2$—$CH_3)$. This group is useful for the properties it gives to the ionic liquid and for its cost and convenience to manufacture.

$R_3$ in structure I above is a substituted or unsubstituted alkylene group, heteroarylene group, arylene group, or cycloalkylene group. Preferably $R_3$ is a substituted or unsubstituted alkylene group and even more preferably $R_3$ is —$(CH_2)_n$— wherein n is an integer of from about one to about 10.

$R_6$, $R_7$, and $R_8$ are independently selected from hydrogen (H) or another substituent such as, for example, alkyl, $NO_2$, halo, cyano, silyl, and OH. Preferably, $R_6$, $R_7$, and $R_8$ are H.

In some instances, two or more adjacent substitutents such as or $R_1$ and $R_2$, $R_4$ and $R_5$, $R_6$ and $R_7$, and/or $R_7$ and $R_8$ may be taken together to form a ring such as a 5-7 membered carbocyclic ring. Examples of such carbocyclic rings include cyclopentyl and cyclohexyl rings.

$R_1$, $R_2$, $R_3$, $R_4$, $R_5$, $R_6$, $R_7$, and $R_8$ may optionally be substituted with one or more substituents. The type of the substituent is not particularly critical so long as the compound or mixture of compounds has the desired ionic liquid properties. Thus, the substituents usually include typical and nontypical organic substituents such as those selected from the group consisting of alkyl, $NO_2$, halo, cyano, silyl, OH, and other suitable substituents. The substituent group itself may often be further branched.

Another exemplary anion that can be used to make ionic liquids is a docusate variant having the following chemical structure:

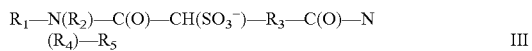

$R_1$, $R_2$, $R_3$, $R_4$, and $R_5$ in chemical structure III can be independently selected from a hydrogen atom (H) or a carbon-containing group, e.g., alkyl, alkenyl, alkynyl, aryl, benzyl, alkyl-ether, etc.

In an embodiment, the anion source is a sodium salt of the 2-ethylhexyl amide sulfonate salt, which can be synthesized using known techniques having the benefit of this Specification. For example, an anion was prepared having the above chemical structure III with $R_1$ and $R_5$ each being a 2-ethylhexyl group, $R_2$ and $R_4$ each being a hydrogen atom, and $R_3$ being a methylene group. Two different ionic liquids were prepared using this anion by first isolating it as a sodium salt and then reacting it with a source of two different cations. The cation in one of the ionic liquids was tetrabutylammonium cation. The cation in the other ionic liquid was 1-methyl-3-hexyl imidazolium.

In other experiments, a second anion was prepared having the above chemical structure III with $R_1$ and $R_5$ each being a 2-ethylhexyl group, $R_2$ and $R_4$ each being an ethyl group, and $R_3$ being a methylene group. Two more ionic liquids were prepared using this anion by first isolating it as a sodium salt and then (in separate experiments) reacting it with a source of the same two cations mentioned above, namely tetrabutylammonium cation and 1-methyl-3-hexyl imidazolium.

Based upon experiments in which ionic liquids have been made from anions having chemical structure III, it is believed that, as is the case with the docusate salts and their derivatives and variants, each of the R groups in chemical structure III could vary in length or composition and still give rise to an ionic liquid when combined with an suitable cation, e.g., an onium cation.

Cations

The cation of the ionic liquid to be produced is not particularly critical so long as the ionic liquid has properties to make it suitable for its intended use. Typical useful cations include, for example, "onium" cations. Onium cations include cations such as substituted or unsubstituted ammonium, phosphonium, and sulfonium cations. Preferred onium cations include, for example, substituted or unsubstituted N-alkyl or N-aryl pyridinium, pyridazinium, pyrimidinium, pyrazinium, imidazolium, pyrazolium, thiazolium, oxazolium, triazolium, imidazolinium, methylpyrrolidinium, isothiazolium, isoxazolium, oxazolium, pyrrolium, and thiophenium. The substituents include one or more of the following groups: halo, alkyl, and aryl groups such as phenyl. In addition, two adjacent substituents may be joined together to form an alkylene radical thereby forming a ring structure converging on N. The alkyl, phenyl, and alkylene radicals may be further substituted. Another particularly preferred cation is an ammonium cation substituted by one or more groups such as alkyl and aryl groups such as phenyl. Many such cations and substituted cations are described in U.S. Pat. Nos. 5,827,602 and 5,965,054, which are incorporated by reference in their entirety.

Other suitable cations include BMIM, tetrabutyl ammonium, tributylmethyl ammonium, tetrabutyl phosphonium, tetraethyl ammonium, N,N-dialkyl pyrrolidinium, trimethyl 2-hydroxyethyl ammonium, N,N'-dialkyl imidazolium, N-alkylpyridinium, or mixtures thereof. The cation may be an onium cation and optionally contains more than 4 carbon atoms.

Processes to Make Compounds Having Structures I-III and Mixtures Thereof

The ionic liquid compounds of structures I-II may be conveniently made by a number of different processes. One process which is suitable for making hydrophobic or hydrophilic ionic liquids or mixtures of the present invention comprises using metathesis, i.e., a double decomposition reaction, whereby the reaction of two or more compounds forms two or more new compounds—one of which is the ionic liquid. For example, reacting [bmim]Cl with sodium docusate will yield [bmim]docusate and NaCl. The two or more compounds produced by the metathesis reaction can then be separated by any means.

The manner of contacting the two or more compounds to form the ionic liquid is not particularly important so long as the desired reaction occurs. Generally, the compounds can be mixed in any order, can be formed in situ, or can be mixed together with a solvent such as water which is at least partially miscible and does not significantly react with any of the compounds.

The starting compounds are often readily available and, in addition, many syntheses are available to those skilled in the art to make the desired starting compounds. The mixing conditions may vary depending on the specific compounds employed and the desired product. In most instances, it is acceptable to contact the compounds and an optional solvent such as water or dichloromethane at ambient pressure and a temperature high enough for the reaction to occur efficiently but not so high as to decompose or boil off any starting compound. Generally, the contacting temperature may range from about 75 to about 110° C., preferably from about 85 to about 100° C. When water is used as a solvent, temperatures of about 75 to about 110° C. are sometimes preferable because this tends to breaks up emulsions which typically form between the ionic liquid and water. On the other hand, when the solvent is organic (e.g., dichloromethane), the preferred temperature is typically substantially lower, usually around room temperature, e.g., 25° C. or slightly above room temperature.

The manner in which the increased temperature is achieved and maintained is not particularly critical. Often any heating element may be employed as the compounds are mixed or the starting compounds can be heated separately and then mixed. Similarly, any vessel or reactor can be employed so long as it is of adequate size and material. Often it is beneficial to employ a stirring means to facilitate the reaction.

Generally, the increased temperature is maintained for at least a sufficient time until the desired reaction has occurred to the desired extent. In some instances, it may be desirable to maintain the increased temperature for a longer time than it takes to complete the reaction. In this manner, any water or lower boiling components that are formed as byproducts or present as solvents can be removed by boiling.

The amount of each of the starting compounds may vary depending upon the desired yield. In general, high yields are often obtained by using about the stoichiometric amount of reactants, i.e., about a 1:1 ratio. However, as one skilled in the art will appreciate, different reaction conditions may alter the ratio of reactants at which the optimum yield occurs.

If one desires to make an ionic liquid mixture comprising two or more different salts, then it can be accomplished by employing a mixture of three or more different compounds so that a variety of salts are formed. The resulting ionic liquid salt mixture can then be used as a mixture or, if desired, individual salts can be separated by routine means.

If necessary, the ionic liquid or ionic liquid mixture may be recovered from the solvent and/or reaction mixture by any suitable means the most efficient of which may vary depending upon the type and desired purity of the ionic liquid or mixture. Suitable means of recovery include rotary evaporation or distillation, azeotropic distillation, ion chromatography, liquid extraction, crystallization, pervaporation, drying agents, and reverse osmosis.

While the aforementioned process may be employed to make hydrophobic or hydrophilic ionic liquids, in some applications it is preferable to make hydrophobic ionic liquids. This is because hydrophobic ionic liquids are often not very soluble in the water which is often used as a reaction medium. Therefore, simple liquid-liquid extraction can be used to separate the hydrophobic ionic liquid from the soluble byproduct. In contrast, hydrophilic ionic liquids are often miscible with the byproduct. Consequently, a different separation method, e.g., solvent extraction, can be employed. For example, it may be desirable or necessary to use a hydrophobic solvent like an alkyl chloride, e.g. methylene chloride, to extract the ionic liquid.

Characteristics and Uses of Ionic Liquids of the Present Invention

The purity of ionic liquids produced by the processes of this invention can often be greater than 55%, preferably greater than 60%, more preferably greater than 70%, most preferably greater than 80%. This is often advantageous for processes that require high purity materials such as in the electronics industry. The ionic liquids are also preferably hydrophobic and thus useful in many processes as a substitute for an organic solvent and in mixtures with catalysts such as $ZnCl_2$, $CuCl_2$, $AlCl_3$, and organic catalysts.

The ionic liquids of the present invention are also often useful in mixtures with hydrocarbons such as alkanes, e.g., hexane. The mixtures often do not hold static electricity charge and thus will not ignite or explode readily.

Docusate and Docusate Variants in Supercritical $CO_2$ Applications

It has been found that tetrabutylammonium docusate is soluble in supercritical carbon dioxide ($CO_2$). Supercritical applications using $CO_2$ typically operate at temperatures between above about 32° C. and pressures above about 1,070 psi. It is believed that the docusate and docusate variant based ionic liquids are useful adjuvants, additives, and detergents for addition to supercritical $CO_2$ for cleaning, synthesis, and separations applications.

Docusate and Docusate Variants as Anti-Static Agents

It is believed that the docusate and docusate variant based ionic liquids are useful antistatic additives for fuel applications and polymer applications. The docusate and docusate variant based ionic liquids tend to be partially or fully miscible with hydrocarbons (e.g., alkanes such as hexane) and can be added to fuels as anti-static additives. These ionic liquids can also be added to polymers, e.g., polyvinylacetate, as an anti-static additive.

Docusate and Docusate Variants in Ionic Liquid Blends

In one embodiment, two or more ionic liquids are blended together to form an improved reaction solvent. It is believed that Lewis Acid ionic liquids can be advantageously blended with ionic liquids based upon docusate or docusate variants to form an improved reaction solvent that provides better mixing between reactants to improve reaction kinetics. Because the docusate and docusate variant ionic liquids tend to be at least relatively miscible with the hydrocarbon streams, they tend to inhibit the formation of two phases and improve the mixing and contact between the reactants. Examples of Lewis Acid ionic liquids that are believed to be useful in making blends with the sulfonate anion (e.g., docusate and docusate variant) ionic liquids of the present invention are disclosed in copending U.S. Application entitled "Lewis Acid Ionic Liquids," filed on Aug. 15, 2003 and invented by Roger Moulton (Ser. No. 10/642,437, and published as US 2004/0122229), which is incorporated by reference as if fully set forth herein.

Exemplary Lewis Acid ionic liquids useful in these blends include ionic liquids having (i) a cation selected from ammonium, sulfonium, and phosphonium cations and having less than 14 total carbon atoms; and (ii) an anion having the formula $Al_yR_{3y+1}$ wherein y is greater than 0 and R is independently selected from the group consisting of an alkyl group and halogen group. A suitable anion for the Lewis Acid ionic liquid in the blend is aluminum chloride anion.

Y may be an integer but it also includes decimals when there are non-stoichiometric amounts of the aluminum anion. In these cases, the aluminum anion will be mixed with other anions such as halides. Thus, ionic liquids of the present inventions include compositions comprising, for example, a quaternary ammonium chloride mixed with a quaternary ammonium aluminum chloride. The aluminum chloride can be, for example, tetrachloroaluminate or heptachlorodialuminate.

The R group and the value of y in the anion are usually selected based on the desired properties of the ionic liquid. For example, if the ionic liquid is going to be used as a Friedel-Crafts catalyst then particularly preferred anions are aluminum chloride anions such as $AlCl_4$ and $Al_2Cl_7$.

When one or more R groups are a halogen group the halogen is preferably chloride, bromide or iodide. When one or more R groups is an alkyl group then the alkyl group should have a sufficient number of carbon atoms so that the ionic liquid has the desired properties. For example, if the ionic liquid is to be used as a catalyst then the total number of carbon atoms in the ionic liquid should be selected so as to maximize the catalyst's effectiveness and efficiency. The total number of carbon atoms may also affect other properties of the ionic liquid such as vapor pressure, dipole moment, polarity, etc.

A suitable cation for the Lewis Acid ionic liquid is tetraalkylammonium. Depending on the desired ionic liquid properties it may be advantageous for one or more of the alkyl groups to be optionally substituted with one or more suitable substitutents. Suitable substituents include, for example, halogens such as chloride, bromide, or iodide. Particularly preferred tetraalkylammonium cations include trimethylethyl ammonium, trimethyl chloromethyl ammonium, trimethylbutyl ammonium, and tributyl methyl ammonium.

Another suitable cation for the Lewis Acid ionic liquid are the N-alkyl substituted saturated heterocycles such as piperidinium and morpholinium. In particular, piperidinium substituted on the nitrogen with an alkoxy or alkyl group such as —$(CH_2)_2$OMe, butyl, or propyl are particularly beneficial. Pyrrolidine-based cations can also be employed. The cation may include ether functionality (e.g., $NCH_2CH_2OCH_3^+$). The cation may include halogenated alkyl groups.

Exemplary Lewis Acid ionic liquids for the blend include ionic liquids having an aluminum chloride anion and a cation sourced from an ammonium salt such as $MeBu_3NCl$, $Me_3PentylNCl$, $Me_3ButylNCl$, $MeEt_3NCl$, $Me_2Et_2NCl$, Cl—$CH_2$—$NMe_3Cl$, or N-methyl-N-Butyl Pyrrolidinium Cl. Other exemplary Lewis Acid ionic liquids include N-alkyl substituted piperidinium heptachlorodialuminate, trimethyl chloromethyl ammonium heptachlorodialuminate, trimethylbutyl ammonium heptachlorodialuminate, and tributyl methyl ammonium heptachlorodialuminate.

The following examples are not intended to limit the invention, but rather, are intended only to illustrate a few specific ways the instant invention may be employed.

Example 1

Synthesis of Tetrabutylammonium Docusate 1 mole sodium docusate (444 grams) was dissolved in 2 liters water, and then 1 mole tetrabutylammonium bromide (321 grams) was added as a solid. After stirring for a few minutes, the stirring was stopped and the solution separated into two layers. The top layer was collected in a separatory funnel. It was washed twice with 1 liter of water, and heated to 100° C. to facilitate phase disengagement. The resulting tetrabutylammonium docusate was heated to 110° C. to drive off any dissolved water in it. The yield was nearly quantitative (624 grams, 94% yield).

Examples 2-5

The ionic liquids of Examples 2-5 in Table 1 below were made substantially as in the same manner as Example 1 except that approximately 1 mole of the starting material in Table 1 was substituted for the 1 mole of tetrabutylammonium bromide in Example 1.

TABLE 1

| Example | Starting Material | Ionic Liquid | Solubility in water |
|---|---|---|---|
| 2 | Me(n-Bu)$_3$N Br | Me(n-Bu)$_3$N Docusate | Hydrophobic |
| 3 | Me$_3$N(CH$_2$)$_6$NMe$_3$ Br | Me$_3$N(CH$_2$)$_6$NMe$_3$ Docusate | Hydrophobic |
| 4 | n-Bu$_4$P Br | n-Bu$_4$P Docusate | Hydrophobic |
| 5 | Et$_4$N Br | Et$_4$N Docusate | miscible |

Examples 6-10

The ionic liquids of Examples 6-10 in Table 2 below were made by dissolving sodium docusate in dichloromethane and in a separate flask dissolving the starting material of Table 2 in dichloromethane. The two solutions were mixed and stirred for approximately 12 hours. The solutions were then filtered to remove precipitated solid salts, then evaporated to thick syrups. The thick syrups are then extracted with diethyl ether, hexanes or a mixture thereof; again filtering to removed solid salts. After rotary evaporation, the residues are redissolved in hexane/ether and the process of filtration repeated (using progressively smaller fractions of ether in the mix) until no further solids were formed. The resulting salts are then washed with water to effect a final removal of inorganic salts, after which they are dried in vacuo.

TABLE 2

| Example | Starting Material | Ionic Liquid |
|---|---|---|
| 6 | 1-n-hexyl-3-methyl imidazolium bromide | 1-n-hexyl-3-methyl imidazolium docusate |
| 7 | 1-n-octyl-3-methyl imidazolium bromide | 1-n-octyl-3-methyl imidazolium bromide docusate |
| 8 | 1-n-butyl-3-methyl imidazolium bromide | 1-n-butyl-3-methyl imidazolium docusate |
| 9 | 1-methyl-2-ethyl imidazolium bromide | 1-methyl-2-ethyl imidazolium docusate |
| 10 | tetra-n-butylammonium bromide | tetra-n-butylammonium docusate |

The ionic liquids of Examples 6-10 were generally hydrophobic ionic liquids. In the case of Example 6, 1-hexyl-3-methyl imidazolium docusate, contacting it with 40 volume percent or less of water resulted in the formation of two phases, even after agitation. However, when 1-hexyl-3-methyl imidazolium docusate was contacted with 50 volume percent water, agitation produced a stiff, visibly monophasic gel. Addition of additional water to the gel, followed by agitation, resulted in the formation of two phases again. While not wishing to be bound by any particular theory, it is believed that some of the ionic liquids of the present invention may become hydrated or solvated when mixed with some proportions of water. This results in an ionic liquid which is insoluble and forms two phases when mixed with some proportions with water and is a single phase at other proportions. This unique behavior could be very beneficial for some applications in which solubility or insolubility with water is important.

Example 11

This example details the synthesis of a tetrabutyl ammonium molten salt of the amide having chemical formula III above. One-tenth of a mole (50 g) of the sodium salt of the amide-sulfonate salt having chemical structure III above (with $R_2$ and $R_4$ being $CH_2CH_3$, $R_1$ and $R_5$ each being a 2-ethylhexyl group, and $R_3$ being $CH_2$) was dissolved in 250 mL of dichloromethane, and one-tenth mole (32 g) of tetrabutyl ammonium bromide was added as a solid. The mixture was stirred for a day, after which time the solution was filtered first through filter paper and then through a short plug of silica gel. The eluted dichloromethane solution was quickly washed with water, dried over magnesium sulfate, and the solvent removed in vacuo, leaving the desired product in high yield (64 g, 89%). The product salt is soluble in both water and in several common organic solvents, such as dichloromethane and acetone. The melting range of the resulting salt was less than about 30° C. because the product was a viscous oil at room temperature. The product salt included Bis (N-ethyl-N-(2-ethylhexyl)sulfosuccinate diamide) anion paired with tetrabutyl ammonium cation.

Examples 12-19

These examples detail the preparation of an ionic liquid from a sodium salt of the sulfosuccinate salts, which are docusate variants. The esters were then combined with an onium cation to make an onium molten salt.

Ten grams (0.03 mol) of tetrabutylammonium bromide was dissolved in 50 mL of water, and to the stirred solution was added as a solid twelve grams (0.03 mol) of the sodium salt of the di-n-hexyl ester of sulfosuccinic acid. (By "di-n-hexyl ester of sulfosuccinic acid" it is meant that the sulfosuccinic acid molecule is esterified on the two carbonyl groups of the sulfosuccinic molecule and not at the sulfonic group). After stirring for a few minutes, the water layer was extracted with three successive 50 mL portions of dichloromethane, which were combined, dried with anhydrous magnesium sulfate, and evaporated, leaving the desired product (13 g, 73% yield). The melting range of the resulting salt was less than about 30° C. because the product was a viscous oil at room temperature.

The same experimental procedure was used to prepare ionic liquids of the tetrabutyl ammonium cation with the sodium salts of the following docusate variants: (i) di-n-cyclohexyl ester of sulfosuccinic acid; (ii) di-n-octyl ester of sulfosuccinic acid; (iii) di-n-butyl ester of sulfosuccinic acid; (iv) di-isobutyl ester of sulfosuccinic acid; (v) di-neopentyl ester of sulfosuccinic acid; (vi) di-n-heptyl ester of sulfosuccinic acid; and (vii) di-n-heptyl ester of sulfosuccinic acid. The melting range of the resulting salts was less than about 80° C. and typically between about 40° C. and 80° C. The octyl and heptyl docusate variants had lower melting ranges as indicated by the fact that they were a viscous liquids at room temperature.

Representative NMR Data

The structure and composition of the ionic liquids was determined by 1H-NMR spectroscopy. For all docusate salts (2-ethylhexylsulfosuccinate diester), the spectra consist simply of resonances arising from the anion superimposed on those of the cation. For all docusate salts, resonances originating from the anion were (with minor variations) within the following ranges: (300 Mhz, CDCl3, d: 0.73-0.83 (triplets), 1.24-1.70 (overlapping multiplets), 3.05-3-31 (complex m), 3.90-4.25 (overlapping m)

Cation resonances (300 MHz, CDCl3, d): (1-methyl-3-hexyl imidazolium): 0.79 (t), 1.21-1.27 (overlapping m), 1.80 (m), 4.03 (s), 4.22 (t), 7.35 (s), 7.49 (s), 9.50 (s).

(tetraethylammonium): 1.32 (t), 3.34 (q)

(tetrabutylammonium): 1.03 (t), 1.20-1.40 (overlapping m), 3.23 (q)

(tetraoctylammonium): 0.86 (t), 1.18-1.50 (overlapping m), 3.25 (q)

(N-methyl-N($CH_2CH_2OCH_2CH_3$) pyrrolidinium): 0.86 (t), 1.31 (m), 2.11 (m), 3.0-4.2 (complex overlapping m)

(trimethylhexadecylammonium): 0.87 (t), 1.20-1.60 (overlapping m), 2.13 (s), 3.15 (q)

(methyltributylammonium): 0.84 (t), 1.23-1.70 (overlapping m), 2.20 (s), 3.24 (m)

(1,2-bis(tributylammonium)ethane): 0.83 (t), 1.22-1.58 (overlapping m), 2.20 (s), 3.22 (m)

Ionic liquids of several docusate variants were also made. The NMR spectra of these salts, like those of the docusate derivatives, consist of the spectrum of the specific anion overlayed on that of the specific cation. Below are the NMR data for the tetrabutylammonium derivatives of three docusate variant salts. For each salt, the resonances arising from the cation comport with those of the tetrabutyl ammonium cation of docusate, the values for which are listed above. Below are the resonances from the anion of these example salts (300 MHz, CDCl3, d):

Bis (n-hexylsulfosuccinate diester): 0.84 (t), 1.2-1.4 (overlapping m), 1.6 (m), 3.07 (m), 4.05-4.22 (overlapping m).

Bis (cyclohexylsulfosuccinate diester): 1.2-1.8 (complex overlapping m), 3.10 (m), 4.2-4.8 (overlapping m)

Bis (neopentylsulfosuccinate diester): 0.87 (s), 0.90 (s), 3.05-3.25 (overlapping m), 3.78 (s), 3.80-3.93 (m), 4.23-4.29 (m)

Bis (N-ethyl-N-(2-ethylhexyl)sulfosuccinate diamide): 0.75-0.88 (triplets), 1.21-1.78 (overlapping multiplets), 2.24 (m) 3.11-3-41 (complex m), 3.86-4.45 (overlapping m)

What is claimed is:

1. An ionic liquid composition, comprising greater than 70 weight percent of an ionic liquid comprising:

(a) a cation independently selected from the group consisting of:

substituted or unsubstituted pyridinium, pyridazinium, pyrimidinium, pyrazinium, imidazolium, pyrazolium, thiazolium, oxazolium, triazolium, imidazolinium, methylpyrrolidinium, isothiazolium, isoxazolium, oxazolium, pyrrolium, and thiophenium, wherein when substituted, the substituent group may be one or more of halo, alkyl, and aryl groups, and two adjacent substituents may be joined together to form an alkylene radical consisting of from about six to about eighteen carbon atoms to form a ring structure converging on N; and quaternary ammonium cation substituted by groups selected from the group consisting of alkyl and aryl groups; and tetrabutyl ammonium, tributylmethyl ammonium, tetrabutyl phosphonium, tetraethyl ammonium, N,N-dialkyl pyrrolidinium, trimethyl 2-hydroxyethyl ammonium, N,N'-dialkyl imidazolium, N-alkylpyridinium, 1-methyl-3-hexyl imadazolium and a mixture thereof; and (b) an anion having the following structure:

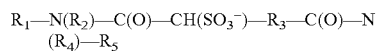

III wherein $R_1$ and $R_5$ are 2-ethylhexyl;

$R_2$ is a hydrogen atom or ethyl;

$R_3$ is a methylene group;

$R_4$ is a hydrogen atom or ethyl; and wherein the ionic liquid has a melting point that is less than about 100° C.

2. The composition of claim 1, wherein $R_1$ is 2-ethylhexyl, $R_2$ is ethyl, $R_3$ is a methylene group, $R_4$ is ethyl, and $R_5$ is 2-ethylhexyl.

3. The composition of claim 2, wherein the cation is tetrabutyl ammonium.

4. The composition of claim 2, wherein the cation is 1-methyl-3-hexyl imidazolium.

5. The composition of claim 1, wherein $R_1$ is 2-ethylhexyl, $R_2$ is a hydrogen atom, $R_3$ is a methylene group, $R_4$ is a hydrogen atom, and $R_5$ is 2-ethylhexyl.

6. The composition of claim 5, wherein the cation is tetrabutyl ammonium.

7. The composition of claim 5, wherein the cation is 1-methyl-3-hexyl imidazolium.

* * * * *